United States Patent [19]

Battilotti et al.

[11] Patent Number: 5,035,791
[45] Date of Patent: Jul. 30, 1991

[54] ION SENSOR CONTAINING A SELECTIVE ORGANIC MEMBRANE

[75] Inventors: Massimo Battilotti; Matteo Giongo, both of Rome, Italy

[73] Assignee: Eniricerche S.p.A., Milan, Italy

[21] Appl. No.: 221,436

[22] Filed: Jul. 19, 1988

[30] Foreign Application Priority Data

Jul. 24, 1987 [IT] Italy ............... 21430 A/87

[51] Int. Cl.$^5$ ............................................. G01N 27/30
[52] U.S. Cl. ................................... 204/415; 204/416; 204/418; 357/25
[58] Field of Search ............... 357/25; 204/415, 416, 204/418, 419

[56] References Cited

U.S. PATENT DOCUMENTS

| | | | |
|---|---|---|---|
| 4,218,298 | 8/1980 | Shimada et al. | 204/418 |
| 4,236,987 | 12/1980 | Schindler et al. | 204/418 X |
| 4,269,682 | 5/1981 | Yano et al. | 357/25 X |
| 4,505,799 | 3/1985 | Baxter | 204/416 |
| 4,735,702 | 4/1988 | Reinhoudt et al. | 204/418 X |
| 4,874,499 | 10/1989 | Smith et al. | 357/25 X |
| 4,878,015 | 10/1989 | Schmidt et al. | 325/71.5 |

Primary Examiner—Nam X. Nguyen
Attorney, Agent, or Firm—Oblon, Spivak, McClelland, Maier & Neustadt

[57] ABSTRACT

An ion sensor is disclosed, together with the relevant process for preparing it, which contains a polymeric organic matrix, a ionophore, a device based on semiconductors of EMOS or ISFET (CHEMFET) type containing at its surface silicon oxide adhering to said polymeric organic matrix by means of a polysiloxanic matrix, characterized in that the polysiloxanic matrix is selected from the organosilanes of general formula

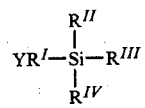

wherein:

$R^{II}$, $R^{III}$, $R^{IV}$, which may be either equal to, or different from, one another, are alkyl or alkoxy groups containing from 1 to 10 carbon atoms, $R^I$ is equal to $(CH_2)_p X (CH_2)_q$ wherein:

X is $CH_2$, or an either mono- or polycondensed aromatic group, or NH or O, p and g, which may be either equal to, or different from, one another, are integers which can have values comprised within the range of from 0 to 10, with value 0 being excluded when X is either NH or O, Y is —$NH_2$ or —OH or —SH, and that the polymeric organic matrix is based on a polymer obtained by reacting a polymerized olefin, whose monomer has the formula:

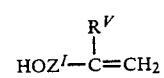

wherein:
$Z^I$ is equal to

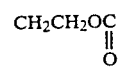

or to $(CH_2)_r$, wherein r is an integer which can have a value comprised within the range of from 1 to 10, $R^V$ can be either H or $CH_3$, with the $CH_3$ value being excluded when $Z^I$ is equal to $(CH_2)_r$, and a compound, obtained by means of the reaction between 2,4-toluene-diisocyanate with a di-alcohol or a di-amine or a glycol or a tri-alcohol or a tri-amine, having the following formula:

(Abstract continued on next page.)

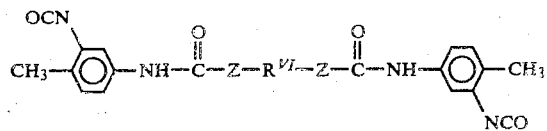 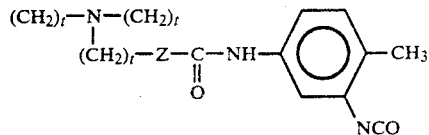

wherein:

$R^{VI}$ is equal to $(CH_2CH_2O)_mCH_2CH_2$, wherein m is an integer which can have values comprised within the range of from 1 to 20,000, or is equal to $(CH_2)_s$, wherein s is an integer which can have values comprised within the range of from 1 to 20, or is equal to wherein t is an integer which can have values comprised within the range of from 1 to 10, and Z can be either —NH— or O, with the —NH— value being excluded when $R^{VI}=(CH_2CH_2O)_mCH_2CH_2$.

6 Claims, 4 Drawing Sheets

ION SENSOR CONTAINING A SELECTIVE ORGANIC MEMBRANE

The present invention relates to the realization of an ion sensor and to the relevant processes of preparation. The selective membrane containing the ion-sensitive species is formed by organic polymeric chains obtained by means of techniques of photo-activation and of thermal treatment.

The ion-sensitive device relevant to the present invention is characterized in that the polymeric organic membrane is kept firmly bound to the insulating layer of $SiO_2$ and $Si_3N_4$ type present on the active part of devices of EMOS (electrolyte membrane oxide semiconductor) or ISFET (CHEMFET) (ion selective field effect transistor) type, by means of stable chemical bonds, by an organic polymeric layer based on reactive polysiloxanes.

These devices which relate to structural elements based on semiconductors can be used in the analytical field, in the diagnostic field, and for the monitoring of toxic substances for environmental protection purposes.

The invention is not only limited to the only structural elements based on semiconductors, but can be applied in the same meaning to other forms of electrodes or devices, compatibly with the techniques of realization of the selective membrane disclosed in the present patent application.

In the field of the conventional electrodes (ISE: ion selective electrodes), the realization of selective membranes of heterogeneous type is normally obtained by dissolving a support polymer, a ionophore and a plasticizer in a suitable solvent.

As the polymeric matrix, normally used is poly(vinyl chloride) (PVC).

The ionophores used can be organic molecules having an open structure (of ETH 227, ETH 1001, ETH 1664 type, and so forth), or having a cyclic structure (of the type of valinomycin, crown-ethers, cryptands, and so forth). Reference is made to a paper published on Analytica Chimica Acta 180, (1986) 299-311. They are capable of forming selectively ion-permeable channels. The membrane obtained, after solvent evaporation, is normally housed on a conventional electrode by using an "O-ring" or other fastening means, with the use thereof being not limited to aqueous solutions.

On the contrary, in case devices of ISFET type are used, the active "gate" portion has dimensions comprised within the range of from 500 to 5,000 $\mu^2$; the deposition, even if at a just physical level, shows to be rather difficult.

Selective membranes of heterogeneous type deposited on CHEMFET are described in "Potassium Ion-Selective Field Effect Transistor" (Anal. Chem. Vol. 47, 13, 2238, 1975), by S. D. Moss, J. Janata and C. C. Johnson. In general, on this subject reference is made to "Recent Advances in Field Effect Chemical Microsensors" by A. Sibbald, J. of Molecular Electropics, Vol. 2, 51-83 (1986) and to "Solid State Chemical Sensors" Acad. Press, London 1985, J. Janata, R. J. Huber.

The most commonly found drawback in this type of electrodes, and in particular for the organic films, is given by the fact that with a long-term use in water, inasmuch as no types of chemical adhesion to the base of the same electrode exist, a swelling, with the consequent detachment of the organic film can occur.

SUMMARY OF THE INVENTION

Accordingly, it is an object of the present invention to provide an ion sensor having a polymeric organic membrane which is firmly bound to the insulating layer of $SiO_2$ and $Si_3N_4$, and which has excellent membrane selectivity.

It is also an object of the present invention to provide an ion sensor which has an ion permeability which can be increased or decreased for a determined ion by the particular chemical composition and structure of the support polymer.

In particular, the above objects and others are provided by an ion sensor, containing an organic polymeric matrix, an ionophore and a device based on an EMOS or ISFET (CHEMFET) semiconductor, containing on its surface silicon oxide adhering to said organic polymeric matrix by means of a polysiloxanic matrix, wherein the polysiloxanic matrix is selected from the organosilanes of the formula:

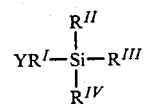

wherein:
$R^{II}$, $R^{III}$ and $R^{IV}$, which are the same or different from each other, are alkyl or alkoxy groups containing from 1 to 10 carbon atoms;
$R^I$ is $-(CH_2)_p X(CH_2)_q-$
wherein:
X is $-CH_2-$ or a mono- or polycondensed aromatic group, or $-NH-$ or $-O-$,
p and q, which are the same or different from each other, are integers having a value of from 0 to 10, with a value of 0 being excluded when X is either $-NH-$ or $-O-$;
Y is $-NH_2$, $-OH$ or $-SH$;
and wherein the polymeric organic matrix is based on a polymer obtained by reacting (1) a polymerized olefin, whose monomer has the formula:

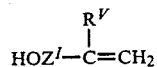

wherein:
$Z^1$ is

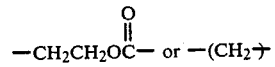

wherein r is an integer having a value of from 1 to 10, and
$R^V$ is either H or $CH_3$, with the proviso that $R^V$ is not $CH_3$ when $Z^I$ is $(-CH_2-)_r$,
with (2) a compound obtained by reacting 2,4-toluene-diisocyanate with a di-alcohol, a d-amine, a glycol, a tri-alcohol or a tri-amine having the formula:

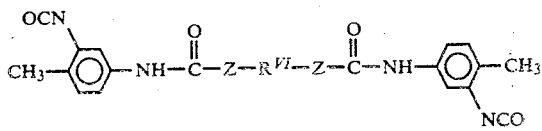

wherein:
$R^{VI}$ is $(-CH_2CH_2O)_m CH_2CH_2-$,
wherein m is an integer having a value of from 1 to 20,000;
or is $(-CH_2-)_s$,
wherein s is an integer having a value of from 1 to 20, or is:

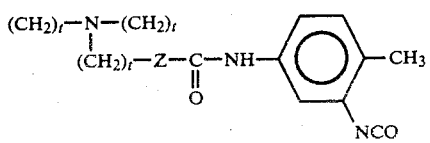

wherein t is an integer having a value from 1 to 10, and Z is $-NH-$ or $-O-$, with the proviso that Z is not $-NH-$ when $R^{VI}$ is $(-CH_2CH_2O)_m CH_2CH_2-$.

Figure 1:
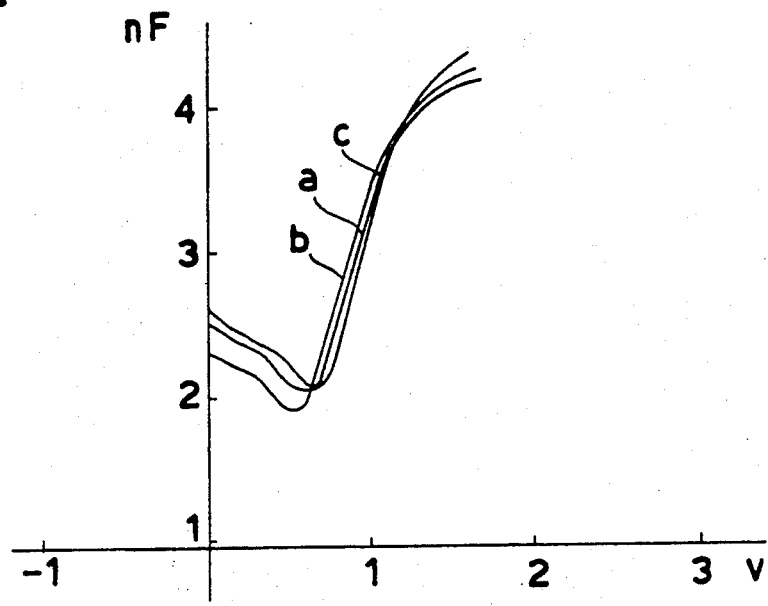
FIGS. 1 and 2 illustrate curves of capacity as a function of the voltage at 120 Hz, respectively, of an EMOS device containing the membrane of the present invention, and of a sample EOS device in the presence of $K^+$ ions (the "a" curve), of $Na^+$ ions (the "b" curve) and of $H^+$ ions (the "c" curve) at $10^{-3}M$ concentration.

In the realization of devices of ISFET type, it is important not to underevaluate the economic viewpoint, and the compatibilization of the technique of deposition and realization of the selective membrane with the techniques of contact terminals application to, and of encapsulation of, the same device.

Furthermore, we regard it important to emphasize how the selection of the constituents of the support polymer may affect the phenomenon of membrane selectivity. In fact, the permeability to a determined ion through the channels of the ionophore can be made more or less easy by the type of chemical composition, and of structure, of the support polymer.

The present Applicant has surprisingly found that by using as the polymeric matrix a polymer obtained from a determined polymerized olefin, and from a compound obtained by reacting 2,4-toluene-diisocyanate and a di-alcohol or a di-amine or a glycol or a tri-alcohol or a tri-amine together with a polysiloxanic matrix selected from determined organosilanes, the stability of the selective membrane is increased, in such a way the long-term use thereof in aqueous solutions being secured.

EMOS or ISFET (CHEMFET) devices with chemically stable selective membranes can be realized in a cheap and simple way by using such techniques as the so-said "spin on" process, and photochemical and thermal treatments of these polymeric films, compatibly with the technologies used in semiconductor field.

The so-said "spin on" process makes it possible slightly viscous solutions to be deposited, with polymeric films being obtained, which may have variable thicknesses of the order of 1 micron, as a function of the added amount of solvent, and of the selected revolution speed (revolutions per minute).

Said layers are subsequently submitted to a photochemical treatment and to a thermal treatment, in order to make it possible stable chemical bonds to form between each other and with the insulating layer based on $SiO_2$ and $Si_3N_4$ of the EMOS or ISFET (CHEMFET) device.

A first object of the present invention is an ion sensor containing an organic polymeric matrix, a ionophore, a device based on semiconductors of EMOS or ISFET (CHEMFET) type, containing on its surface silicon oxide adhering to said organic polymeric matrix by means of a polysiloxanic matrix, characterized in that said polysiloxanic matrix is selected from the organosilanes of general formula:

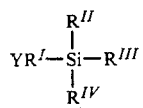

wherein:
$R^{II}$, $R^{III}$, $R^{IV}$, which can be either equal to, or different from, one another, are alkyl or alkoxy groups containing from 1 to 10 carbon atoms,
$R^I = (CH_2)_p X (CH_2)_q$
wherein:
X is $CH_2$, or an either mono- or polycondensed aromatic group, or NH or O,
p and q, which may be either equal to, or different from, one another, are integers which can have a value comprised within the range of from 0 to 10, with value 0 being excluded when X is either NH or O,
Y is either $-NH_2$ or $-OH$ or $-SH$,
and that the polymeric organic matrix is based on a polymer obtained by reacting a polymerized olefin, whose monomer has the formula:

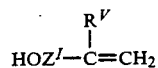

wherein:
$Z^I$ is equal to

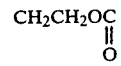

or to $(CH_2)_r$,
wherein is an integer which can have values comprised within the range of from 1 to 10,
$R^V$ can be either H or $CH_3$, with the $CH_3$ value being excluded when $Z^I$ is equal to $(CH_2)_r$,
and a compound, obtained by means of the reaction between 2,4-toluene-diisocyanate and a di-alcohol or a di-amine or a glycol or a tri-alcohol or a tri-amine, having the following formula:

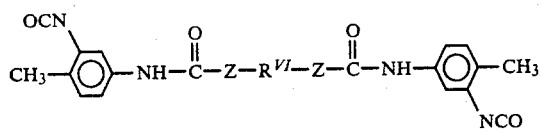

wherein:
$R^{VI}$ is equal to $(CH_2CH_2O)_m CH_2CH_2$, wherein m is an integer which can have values comprised within the range of from 1 to 20,000,
or is equal to $(CH_2)_s$,
wherein s is an integer which can have values comprised within the range of from 1 to 20, or is equal to

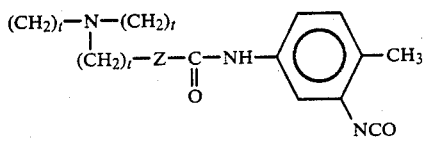

wherein
t is an integer which can have values comprised within the range of from 1 to 10, and
Z can be either —NH— or O, with the —NH— value being excluded when $R^{VI} = (CH_2CH_2O)_m CH_2CH_2$.

The structure obtained from the polysiloxanic matrix, the organic polymeric matrix and silicon oxide present on the surface of EMOS or ISFET (CHEMFET) device can be schematically depicted as follows:

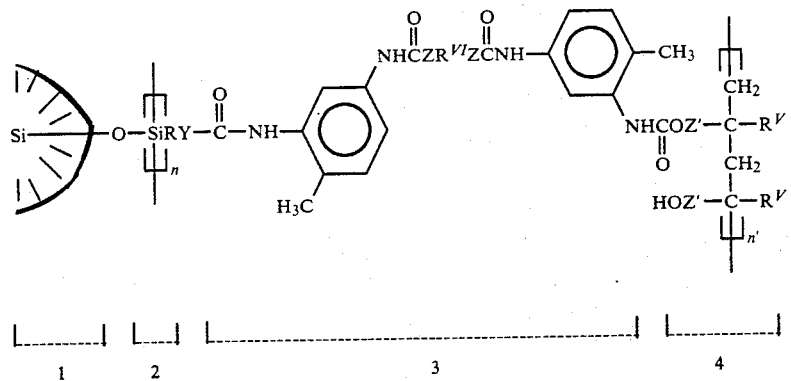

In case $R^{VI}$ is equal to

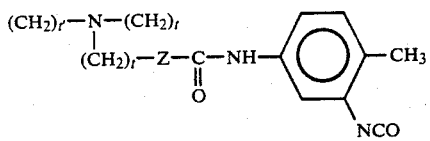

the third isocyanate function will bind itself to a new moiety represented by the reference numeral (4), with a higher crosslinking degree of the polymer being obtained. (n and n' are integers which can have values comprised within the range of from 100 to 10,000).

By the above reference numerals, indicated are:
by 1 silicon oxide;
by 2 the polysiloxanic matrix;
by 3 the organic polymeric matrix based on 2,4-toluenediisocyanate:
by 4 the polymeric matrix based on a polymerized olefin.

As the polysiloxanic matrices, for example, aminoethyl-aminopropyl-trimethoxy-silane (AEAPS) or aminoethyt-aminomethyll-phenetyl-trimethoxy-silane (AEAMPS) can be used.

As the ionophores, open-structure organic molecules (of, e.g., ETH 227, ETH 1001, ETH 1644, etc., type) or cyclic-structure organic molecules (of the type of, e.g., valinomycin, crown-ethers, cryptands, etc.) can be used. The device of EMOS type, besides containing silicon oxide, and, possibly, silicon nitride, on its surface, should contain, in its portion under the same silicon, a layer of aluminum or gold deposited by evaporation.

For example, as the organic polymeric matrix, 2-hydroxyethylmethacrylate and a compound obtained by reaction between 2,4-toluene-diisocyanate and triethylene-glycol or triethanolamine can be used.

Another object of the present invention consists in the process for obtaining the ion sensor.

A first process can be carried out by means of the following process steps:
preparation of a siloxanic prepolymer, followed by one or more deposition(s) of the same siloxanic prepolymer on a device of either EMOS or ISFET (CHEMFET) type;
preparation and deposition on the siloxanic prepolymer of a solution containing a ionophore, a monomer of an olefin polymerizable by means of U.V. light with the formation of $(-C-C-)_{n'}$, bonds, wherein n' is an integer which can have values comprised within the range of from 100 to 10,000, a compound obtained by means of the reaction between 2,4-toluene-diisocyanate and a di-alcohol or a di-amine or a glycol or a tri-alcohol or a tri-amine, followed by a thermal treatment (a "thermal curing"), so as to form stable chemical bonds of —O—CO—NH— urethanic type or of —NH—CO—NH— ureidic type, in order to obtain the physical entrapment of the ionophore, and so as to cause the polymerization to take place by hydrolysis of the alkoxy groups of the silane, with a polysiloxanic matrix, and the consequent chemical bonding of said matrix to silicon oxide, being obtained owing to the reaction of further alkoxy groups with the Si—OH hydroxy groups existing on the oxidated surface. Besides the above disclosed reactions, also such a reaction between the diisocyanate-based compound and the polysiloxanic matrix takes place, as to form a single chemical structure bonded to the insulating layer of the device.

A second process can be carried out by means of the following steps:

preparation of a siloxanic prepolymer, followed by one or more deposition(s) of same siloxanic prepolymer on a device of either EMOS or ISFET (CHEMFET) type;

preparation of a solution containing a ionophore, a monomer of a polymerizable olefin, 2,4-tolueneisocyanate and a di-alcohol or a di-amine or a glycol or a tri-alcohol or a tri-amine, followed, after said solution being kept stirred for at least 48 hours at room temperature, by the deposition thereof on the siloxanic prepolymer, by a photochemical treatment which causes the monomer of the olefin to polymerize by means of U.V. light with the formation of $(-C-C-)_{n'}$ bonds, wherein n' is an integer which can have values comprised within the range of from 100 to 10,000, and by a thermal treatment (a "thermal curing"), so as to form stable chemical bonds of $-O-CO-NH-$ urethanic type or of $-NH-CO-NH-$ ureidic type, in order to obtain the physical entrapment of the ionophore, and so as to cause the polymerization to take place by hydrolysis of the alkoxy groups of the silane, with a polysiloxanic matrix, and the consequent chemical bonding of said matrix to silicon oxide, being obtained owing to the reaction of further alkoxy groups with the Si—OH hydroxy groups existing on the oxidated surface.

The depositions of the siloxanic prepolymer and of the solution containing the membrane constituents and the ionophore, are carried out, in both above cited processes, by means of the so-said "spin-on techniques", i.e., using a rotary-disk equipment. The excess of deposited solution is removed by centrifugation owing to the revolutionary movement of the disk. Then, the solvent evaporates from the solution, and the concerned compound(s) polymerize(s) and react(s) owing to the effect of the thermal and photochemical treatments.

The thermal treatments of the siloxanic pre-polymer and of the solution containing the components of the selective membrane deposited on the polysiloxanic layer are preferably carried at a temperature comprised within the range of from 40° to 200° C., preferably of from 80° to 150° C. The photochemical treatment is carried out by means of U.V. light, e.g., with a mercury lamp (HBO 100/W 2 type).

The thickness of deposited siloxanic prepolymer should be comprised within the range of from 0.1 to $10\mu$ preferably of from 0.5 to $3\mu$, whilst the thickness of the solution containing the membrane should have a thickness comprised within the range of from 0.1 to $100\mu$, preferably of from 10 to $30\mu$.

The revolution speed for the depositions with a spin-on equipment should be comprised within the range of from 500 to 6,000 rpm, and preferably of from 3,500 to 5,500 rpm.

The above disclosed prepolymer makes it possible devices to be obtained, wherein the ionophore is physically entrapped in the membrane obtained by polymerizing the components of the solution.

The photochemical treatment can be possibly carried out in the presence of a free-radical photoinitiator.

Some examples are given now in order to better illustrate the invention, without however limiting it.

EXAMPLE 1

A device of EMOS type, sensible to potassium ions was prepared by means of the above disclosed process.

On oxide/semiconductor structures of $0.5 \times 0.5$ cm of size (Si of "p" type, $\rho = 5-10 \Omega$, orientation 100, oxide thickness 500 Å), a solution was deposited, which contained a partially hydrolysed organosilane in a water-alcohol medium, containing:

21% of 3-[(2-aminoethyl)amino]propyl-trimethoxysilane;

3% of acetic acid;

1% of water.

The deposition was carried out by means of a rotary-disk apparatus running at a revolution speed of 5,000 rpm for 30 seconds (spin-coating). A second deposition was then carried out by means of the same technique, of a slightly viscous solution obtained as follows:

the solution which contained the toluene-diisocyanate-based compound, obtained as follows:

a) tetrahydrofuran: 2 ml b) 2,4-toluene-diisocyanate: 1.5 ml c) triethylene-glycol: 0.7 ml was prepared, and and was kept stirred for 72 hours at the temperature of 25° C.;

to this solution d) 2-hydroxyethyl-methacrylate: 2 ml was slowly added dropwise and the whole solution was kept stirred for 8 hours at the temperature of 25° C.;

to 1 ml of this solution, 30 mg of valinomycin was added.

The deposition of this solution took place by the spin-on technique at 5,000 rpm for 30 seconds.

The samples were submitted to the action by U.V. light for a 3-hour time, with the lamp being placed at a distance of 25 cm from the samples. In this way, the complete polymerization of methacrylate was achieved.

The samples were then submitted to a second treatment of thermal type at 120° C. for a 16-hour time. In this way, the complete condensation between the —OH groups of methacrylate and of the aminosilane with the —NCO groups of the compound obtained by reacting toluenediisodyanate with triethylene-glycol was obtained.

Furthermore, the complete polymerization of the prehydrolysed organosilane and the reaction of the alkoxysilyl groups with the —SiOH groups of silicon oxide took place. The result was a complete chemical anchorage of the selective membrane to the device.

Figure 2:
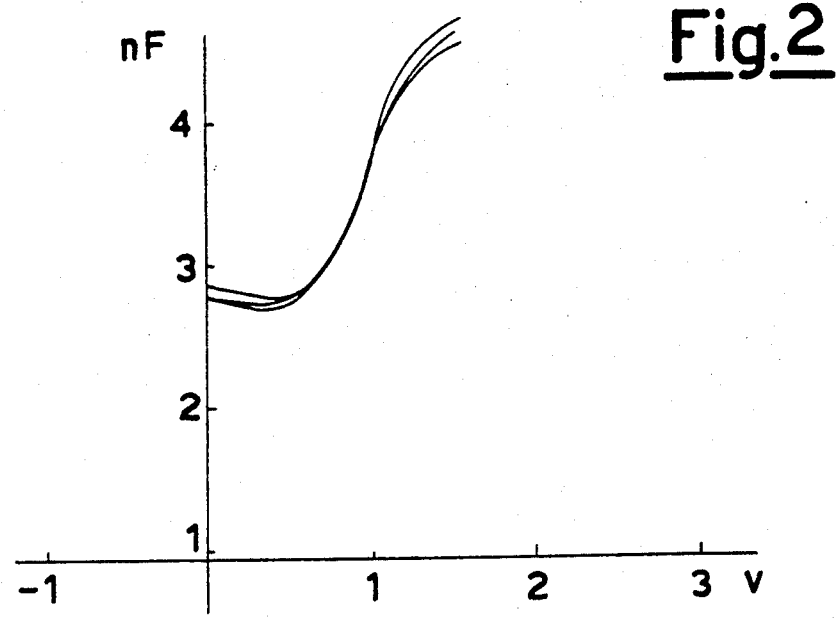

Reported in FIGS. 1 and 2 are the curves of capacity as a function of the voltage at 120 Hz respectively of an EMOS device containing the membrane, and of a simple EOS device in the presence of $K^+$ ions (the "a" curve), of $Na^+$ ions (the "b" curve) and of $H^+$ ions (the "c" curve) at a $10^{-3}M$ concentration. The capacity/voltage (C/V) curves in these structures are taken into consideration in semiconductor technology generally as a test for function of the corresponding field-effect transistors. In fact, the position of the C/V curves is directly related to the threshold voltage of the transistors produced by means of the same technologies.

It can be observed that, whilst in FIG. 2 no shifts of device capacity curves are observed in the presence of $K^+$, $Na^+$, $H^+$, in FIG. 1 the univocal shift is observed of the capacity curves towards positive voltage values as a function of the position of the cation in the selectivity series. This shift corresponds to the same value of variation of the threshold voltage of an ISFET having an analogous structure.

Figure 3:
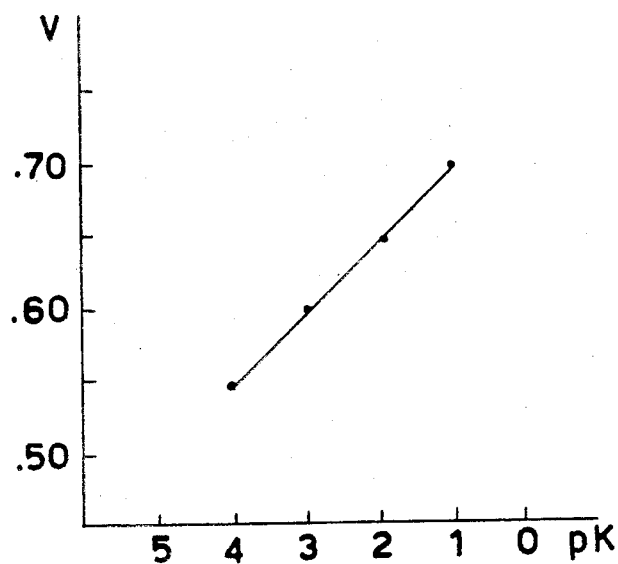
FIG. 3 illustrates the voltage values (as V) which are reported as a function of increasing concentrations of $K^+$.

In FIG. 3, the voltage values (as V) are reported as a function of increasing concentrations of $K^+$ ($pK = -\log[K^+]$). A linear trend with values of 52 mV per decade between $10^{-1}$ and $10^{-4}$M of $K^+$ is obtained.

Figure 4:
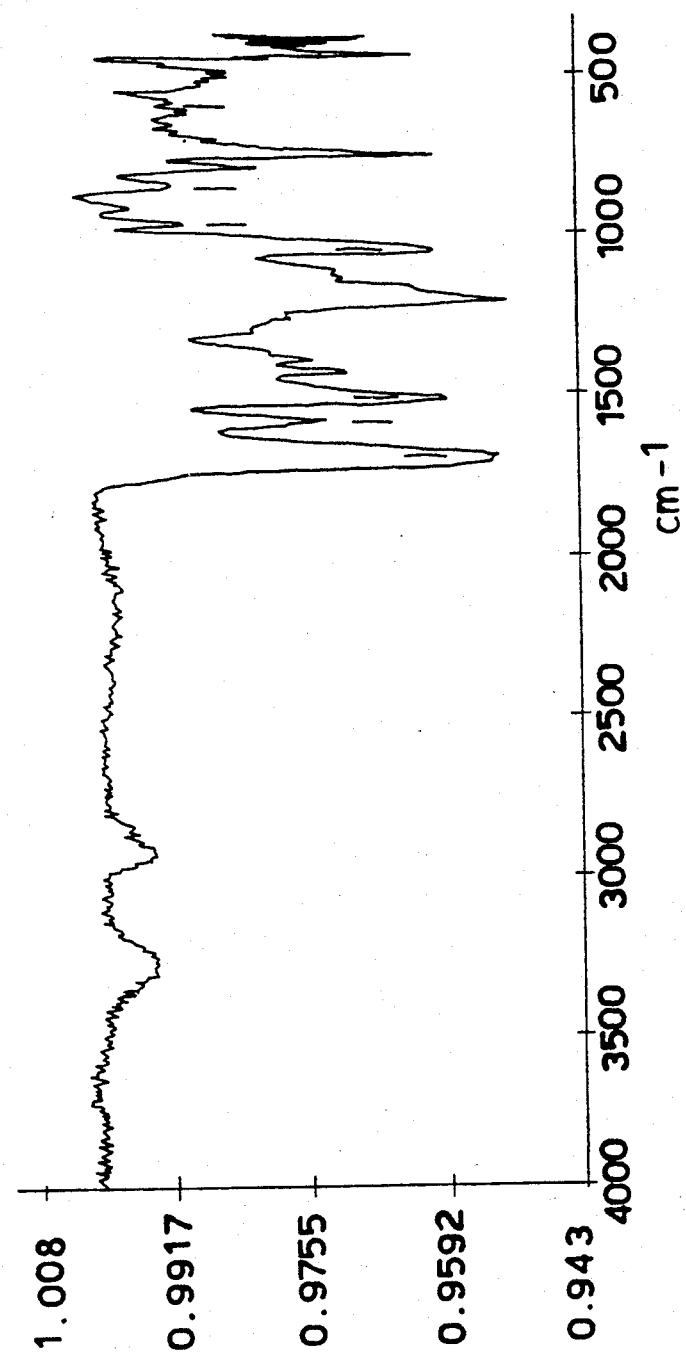
FIG. 4 illustrates an infrared spectrum in Fourier transform.

In FIG. 4, a typical I.R. spectrum in Fourier transform (FTIR) is reported (wherein on the abscissa the wave numbers in $cm^{-1}$ are represented), which was obtained on an EMOS device in transmission. There can be observed:

the absence of the absorption relevant to the stretching of the $-C=C-$ double bond at 1,637 $cm^{-1}$, which confirms the occurred polymerization of the methacrylate;

the absence of the absorption relevant to the stretching of the -NCO group between 2,275 and 2,240 $cm^{-1}$, confirming that the reaction of condensation with the alcoholic and amino groups is complete;

presence of a complex band relevant to the absorptions of the urethanic $-NHCOO-$ bond and of the ureidic $-NHCONH-$ bonds formed after the thermal treatment, comprised between 1,700 and 1,705 $cm^{-1}$;

the presence of a band relevant to the absorption of the $-COC-$ bonds at 1,217 $cm^{-1}$, typical for triethyleneglycol;

the presence of a band relevant to the absorption of the siloxanic $-SiOSi-$ bonds at 1,061 $cm^{-1}$ of the polymerized organosilane.

Figure 5:
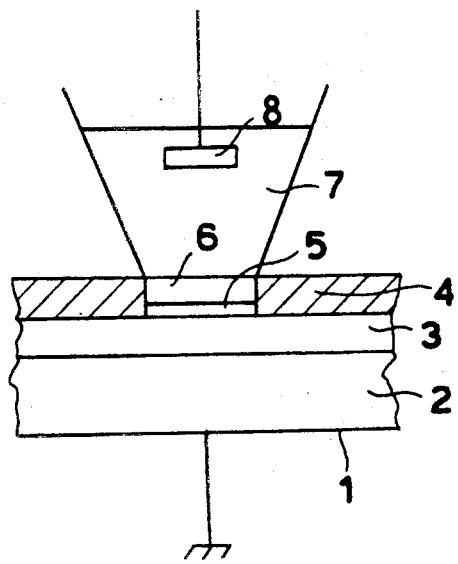
FIG. 5 schematically illustrates a EMOS device including selective membranes of the present invention.
Figure 6:
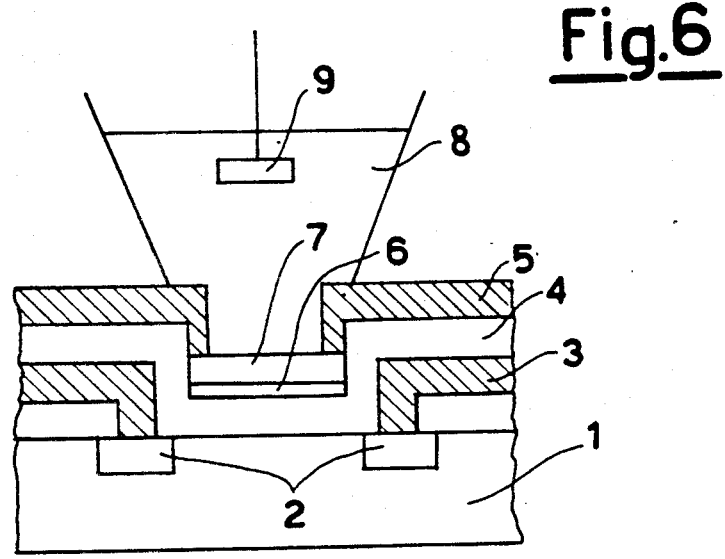
FIG. 6 illustrates an ISFET device complete with the selective membrane.
Figure 7:
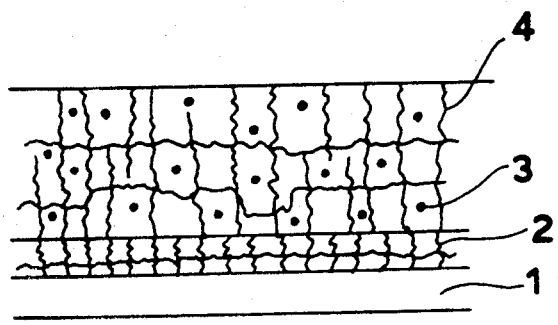
FIG. 7 illustrates the selective membrane of the present invention.

In FIG. 5, an EMOS device complete with the selective membrane is schematically depicted, with the meaning of the reference numerals being the following:

1 aluminum
2 silicon
3 silicon oxide
4 encapsulating material
5 polysiloxane
6 polymer+ionophore
7 solution
8 reference electrode In FIG. 6, an ISFET device complete with the selective membrane and encapsulated is schematically depicted, with the meaning of the reference numerals being the following:

1 silicon
2 source and drain
3 contacts
4 silicon oxide
5 encapsulating material
6 polysiloxane
7 polymer+ionophore
8 solution
9 reference electrode In FIG. 7 the selective membrane is schematically depicted in greater detail, with the meaning of the reference numerals being the following:

1 silicon oxide
2 polysiloxanic matrix
3 ionophore
4 support polymer

EXAMPLE 2

A $K^+$-ion-selective device of ISFET type containing the membrane of the present invention was prepared.

On a FET device without contact terminals, containing a membrane gate and a reference gate of the dimensions 2.3 mm×3.1 mm, the following operations were carried out:

Mechanical masking of the area of the contacts provided on the device, with a suitable special, adhesive tape resistant to heat and to the photochemical treatment;

Deposition on the gate of a solution containing an organosilane, partially hydrolysed in a water-alcoholic medium constituted by:
21% of 3-[(2-aminoethyl)-amino]propyl-trimethoxysilane;
3% of acetic acid;
1% of water,
in absolute ethanol.

The deposition was carried out by means of a rotary-disk equipment revolving at 5,000 rpm for 30 seconds (spin-coating);

Deposition of a slightly viscous solution obtained as follows:
The solution containing the diisocyanate-based compound, which compound was obtained as follows:
a) tetrahydrofuran: 2 ml
b) 2,4-toluene-diisocyanate: 1.5 ml
c) triethylene-glycol: 0.7 ml
is prepared and is kept stirred for 72 hours at the temperature of 25° C.;
To this solution added is:
d) 2-hydroxy-ethyl-methacrylate: 2 ml
and the solution is kept stirred for approximately 8 hours at the temperature of 25° C.;
To 1 ml of this so-obtained solution 30 mg of valinomycin (by FLUKA) is added.

The deposition is carried out by means of the spin-coating technique at 5,000 rpm for 30 seconds. The device is submitted to the effect of U.V. light for a 3-hour time, with the lamp being maintained at a distance of approximately 25 cm from the samples. In this way, the complete polymerization of methacrylate is obtained. The device is subsequently submitted to a treatment of thermal type at 120° C. for a time of 16 hours. In this way, the complete condensation between the $-OH$ groups of methacrylate and of the amino-silane with the $-NCO$ groups of the compound obtained by reacting toluene-diisocyanate with triethylene-glycol is obtained. Furthermore, the complete polymerization of the pre-hydrolysed organosilane and the reaction of the alkoxide groups with the $-SiOH$ groups of silicon oxide are obtained. The result is a complete chemical anchoring of the selective membrane to the device;

Mechanical removal of the adhesive layer used as the mask for the deposition of the membrane;

Housing of the device on a commercial metal support of TO5 type;

Application of the contacts of the device on the support, by using an ultra-sound microwelder;

Masking of the area wherein the selective membrane is present;

Deposition of a suitable encapsulating material on the device provided with the contacts, and on the support;

Mechanical removal of the masking material present on the membrane.

Figure 8:
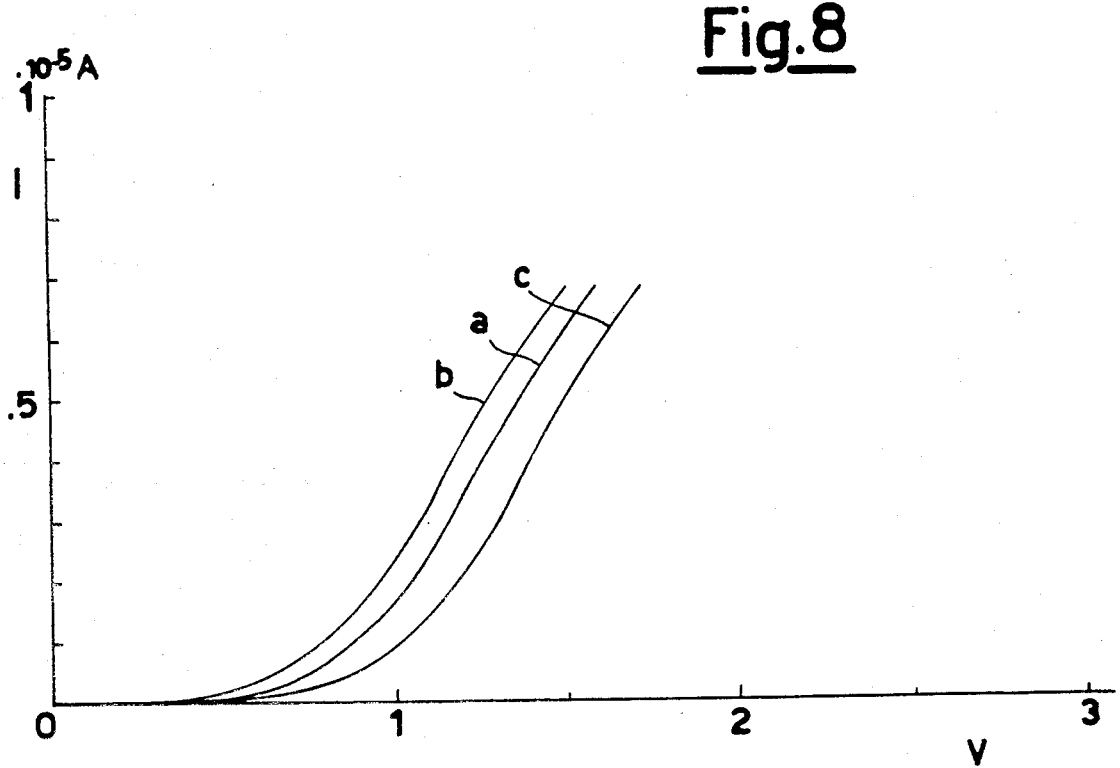
FIG. 8 illustrates the I/V chart of an ISFET device.

In FIG. 8, the I/V chart is reported, which relates to an ISFET device with a constant drain V=5. The threshold shifts relevant to solutions containing $10^{-3}$M $K^+$ (the (a) line), $Na^+$ (the (b) line) and $H^+$ ions (the (c) line) can be observed.

EXAMPLE 3

The same $K^+$-ion-selective device of ISFET disclosed in Example 2, containing the membrane of the present invention, obtained by means of a different photopolymerization technique, was prepared.

On a dual-gate FET device without contact terminals, containing a membrane gate and a reference gate of dimensions of 2.3 mm × 3.1 mm, the following operations were carried out:

Mechanical masking of the area of the contacts provided on the device, with a suitable special, adhesive tape resistant to heat and to the photochemical treatment;

Deposition on the gate of a solution containing an organosilane, partially hydrolysed in a water-alcoholic medium, after leaving the solution, constituted by:
21% of 3-[(2-aminoethyl)-amino]propyl-trimethoxysilane;
3% of acetic acid;
1% of water,
in absolute ethanol, standing for 48 hours. The deposition was carried out by means of a rotary-disk equipment revolving at 5,000 rpm for 30 seconds (spin-coating);

Deposition of a slightly viscous solution, obtained in the following way:
The solution containing the diisocyanate-based compound, which compound was obtained as follows:
a) tetrahydrofuran: 2 ml
b) 2,4-toluene-diisocyanate: 1.5 ml
c) triethylene-glycol: 0.7 ml
is prepared and is kept stirred for 72 hours at the temperature of 25° C.;

To this solution added was:
d) 2-hydroxy-ethyl-methacrylate: 2 ml
and the solution was kept stirred for approximately 8 hours at the temperature of 25° C.;

To 1 ml of this so-obtained solution 30 mg of valinomycin (by FLUKA), and 1% of 2,2-diethoxy-acetophenone, to be used as the photoinitiator were added.
The deposition was carried out by means of the spin-coating technique at 5,000 rpm for 30 seconds.
The deposition process was repeated twice.

The device was submitted to the effect of U.V. light for a 5-minute time, with the lamp being maintained at a distance of approximately 25 cm from the samples. In this way, the complete polymerization of methacrylate was obtained. The device was subsequently submitted to a second treatment of thermal type at 120° C. for 16 hours. In this way, the complete condensation between the —OH groups of methacrylate and of the amino-silane with the —NCO groups of the compound obtained by reacting toluenediisocyanate with triethylene-glycol was obtained. Furthermore, the complete polymerization of the prehydrolysed organosilane and the reaction of the alkoxide groups with the —SiOH groups of silicon oxide were obtained. The result was a complete chemical anchoring of the selective membrane to the device;

Mechanical removal of the adhesive layer used as the mask for the deposition of the membrane;

Housing of the device on a commercial metal support of TO5 type;

Application of the contacts of the device on the support, by using an ultra-sound microwelder;

Masking of the area wherein the selective membrane is present;

Deposition of a suitable encapsulating material on the device provided with the contacts, and on the support;

Mechanical removal of the masking material present on the membrane.

The same procedure of realization of this membrane can be repeated on EMOS devices too, by following the route as disclosed in Example No. 1.

From the electrochemical measurements carried out in aqueous solutions, it resulted that the ISFET containing the membrane according to the present invention is more sensitive to potassium ions than the device of Example 2, while maintaining unchanged its selectivity towards other ions.

EXAMPLE 4

An ISFET device was prepared, which contained the membrane of the present invention, wherein as the ionophore, N,N-dibutyl-3,6-dioxa-octane-diamide was used, which was prepared as reported by the specialized literature on Analytical Chemistry, 1984, 56, 1127-1131, and from a more general standpoint on Ion-Selective Microelectrodes, D. Ammann, 1986, Springer-Verlag, New York.

On a dual-gate FET device without contact terminals, containing a membrane gate and a reference gate of the dimensions 2.3 mm × 3.1 mm, the following operations were carried out:

Mechanical masking of the area of the contacts provided on the device, with a suitable special, adhesive tape (Scotch, 3M, 92) resistant to heat and to the photochemical treatment;

Deposition on the gate of a solution, kept stirred at room temperature for 48 hours, containing an organosilane, partially hydrolysed in a water-alcoholic medium, constituted by:
21% of 3-[(2-aminoethyl)-amino]propyl-trimethoxysilane;
3% of acetic acid;
1% of water,
in absolute ethanol.
The deposition was carried out by means of a rotary-disk equipment revolving at 5,000 rpm for 30 seconds (spin-coating);

Deposition of a slightly viscous solution, obtained in the following way:
The solution containing the diisocyanate-based compound, which compound was obtained as follows:
a) tetrahydrofuran: 2 ml
b) 2,4-toluene-diisocyanate: 1.5 ml
c) triethylene-glycol: 0.7 ml
is prepared and is kept stirred for 72 hours at the temperature of 25° C.;

To this solution added was:
d) 2-hydroxy-ethyl- methacrylate: 2 ml
and the solution was kept stirred for approximately 8 hours at the temperature of 25° C.;

To 1 ml of this so-obtained solution, 50 μ of N,N-dibutyl-3,6-dioxaoctane-diamide and 1% of 2,2-diethoxy-aceto-phenone, to be used as the photoinitiator in methacrylate polymerization, were added.
The deposition was carried out by means of the spin-coating technique at 5,000 rpm for 30 seconds.
The deposition process was repeated twice.

The device was submitted to the effect of U.V. light for a 5-minute time, with the lamp being maintained at a distance of approximately 25 cm from the samples. In this way, the complete polymerization of methacrylate was obtained.

The device was subsequently submitted to a second treatment of thermal type at 120° C. for a 16-hour time. In this way, the complete condensation between the —OH groups of methacrylate and of the aminosilane with the —NCO groups of the compound obtained by reacting toluene-diisocyanate with triethyleneglycol was obtained. Furthermore, the complete polymerization of the pre-hydrolysed organosilane and the reaction of the alkoxide groups with the —SiOH groups of silicon oxide was obtained. The result is a complete chemical anchoring of the selective membrane to the device;

Mechanical removal of the adhesive layer used as the mask for the deposition of the membrane;

Housing of the device on a commercial metal support of T05 type;

Application of the contacts of the device on the support, by using an ultra-sound microwelder;

Mechanical masking of the area wherein the selective membrane is present;

Deposition of a suitable encapuslating material on the device provided with the contacts, and on the support;

Mechanical removal of the masking material present on the membrane.

The electrochemical response of the ISFET device realized with the membrane according to the present invention, obtained in a PbNO$_3$ solution, relates to a system with a flow-cell, with the values of $V_d$ and $V_g$ being maintained constant and measuring the variation of the current in time. A change in drain current of approximately 7 $\mu$A as measured, which corresponds to a change of 70 mV in the threshold voltage at a $10^{-4}$ M concentration of PbNO$_3$ in H$_2$O at ph 7.

The same procedure of realization of this membrane with this ionophore as reported in the instant Example can be repeated on EMOS devices too, by following the route disclosed in Example No. 1, with the necessary modifications in the preparation conditions being taken into due account.

EXAMPLE 5

This example illustrates a method of preparation of the membrane according to the present invention by means of an initial pre-curing of the siloxanic layer.

A K$^+$-ion-sensitive ISFET device was prepared, which contained the membrane of the present invention, wherein as the ionophore, valinomycin was used.

On a dual-gate FET device without contact terminals, containing a membrane gate and a reference gate of 2.3 mm × 3.1 mm of dimensions, the following operations were carried out:

Mechanical masking of the area of the contacts provided on the device, with a suitable special, adhesive tape resistant to heat and to the photochemical treatment;

Deposition on the gate of a solution containing an organosilane, partially hydrolysed after a 48-hour stirring in a water-alcoholic medium, constituted by:
21% of 3-[(2-aminoethyl)-amino]propyl-trimethoxysilane;
3% of acetic acid;
1% of water,
in absolute ethanol.

The deposition was carried out by means of a rotary-disk equipment revolving at 5,000 rpm for 30 seconds (spin-coating);

Thermal pre-curing at 150° C. for 20 minutes;

Deposition of a slightly viscous solution, obtained in the following way:

The solution containing the diisocyanate-based compound, which compound was obtained as follows:
a) tetrahydrofuran: 2 ml
b) 2,4-toluene-diisocyanate: 1.5 ml
c) triethylene-glycol: 0.7 ml
is prepared and is kept stirred for 72 hours at the temperature of 25° C.;

To this solution added was:
d) 2-hydroxy-ethyl-methacrylate: 2 ml
and the solution was kept stirred for approximately 8 hours at the temperature of 25° C.;

To 1 ml of this so-obtained solution 30 mg of valinomycin (a FLUKA product) and 1% of 2,2-diethoxy-aceto-phenone, to be used as the photoinitiator were added.

The deposition was carried out by means of the spin-coating technique at 5,000 rpm for 30 seconds.

The deposition process was repeated twice.

The device was submitted to the effect of U.V. light for a 5-minute time, with the lamp being maintained at a distance of approximately 25 cm from the samples. In this way, the complete polymerization of methacrylate was obtained.

The samples were subsequently submitted to a second treatment of thermal type at 120° C. for 16 hours. No leakages, of any types, of the polymeric material and of valinomycin were observed when the device was kept in an aqueous solution over more than 2 months at room temperature (U.V. spectrophotometric check).

EXAMPLE 6

An example of realization of the ISFET is disclosed, which was carried out by depositing the membrane of the present invention on an already encapsulated device.

A dual-gate FET device containing a membrane gate and a reference gate was housed on a commercial support of TO$_5$ type; the following operations were then carried out:

Application of the contacts of the device on the support, by using an ultra-sound microwelder;

Masking of the area wherein the selective membrane was present;

Deposition of a suitable encapsulating material on the contact-bearing device and on the support, with the device gate area being suitably covered;

Mechanical removal of the protection on the gate;

Deposition on the gate of a solution containing an organosilane, partially hydrolysed in a water-alcoholic medium, after keeping the solution stirred for 48-hours, constituted by:
21% of 3- [(2-aminoethyl)-amino]propyl-trimethoxysilane;
3% of acetic acid;
1% of water, The deposition was carried out by means of a rotary-disk equipment revolving at 5,000 rpm for 30 seconds (spin-coating);

Deposition of a slightly viscous solution, obtained in the following way:

The solution containing the diisocyanate-based compound, which compound was obtained as follows:
a) tetrahydrofuran: 2 ml
b) 2,4-toluene-diisocyanate: 1.5 ml
c) triethylene-glycol: 0.7 ml
is prepared and is kept stirred for 72 hours at the temperature of 25° C.;
To this solution added was:
d) 2-hydroxy-ethyl-methacrylate: 2 ml
and the solution was kept stirred for approximately 8 hours at the temperature of 25° C.;
To 1 ml of this so-obtained solution, 30 mg of valinomycin (a product by FLUKA) and 1% of 2,2-diethoxy-aceto-phenone, to be used as the photoactivator, were added.
The deposition was carried out by means of the spin-coating technique at 5,000 rpm for 30 seconds.
The deposition process was repeated twice.
The device was submitted to the effect of U.V. light for a 5-minute time, with the lamp being maintained at a distance of approximately 25 cm from the samples. In this way, the complete polymerization of methacrylate was obtained.
The device was subsequently submitted to a second treatment of thermal type at 120° C. for 12 hours. In this way, the complete condensation between the —OH groups of methacrylate and of the amino-silane with the —NCO groups of the compound obtained by reacting toluene-diisocyanate with triethylene-glycol was obtained. Furthermore, the complete polymerization of the pre-hydrolysed organosilane and the reaction of the alkoxide groups with the —SiOH groups of silicon oxide were obtained. The result was a complete chemical anchoring of the selective membrane to the so-encapsulated device.

We claim:

1. An ion sensor, containing an organic polymeric matrix, an ionophore and a device based on an EMOS or ISFET (CHEMFET) semiconductor, containing on its surface silicon oxide adhering to said organic polymeric matrix by means of a polysiloxanic matrix, wherein said polysiloxanic matrix is selected from the organosilanes of the formula:

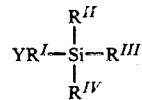

wherein:
$R^{II}$, $R^{III}$ and $R^{IV}$, which are the same or different from each other, are alkyl or alkoxy groups containing from 1 to 10 carbon atoms;
$R^I$ is —(CH$_2$)$_p$ X (CH$_2$)$_q$—
wherein:
X is —CH$_2$— or a mono- or polycondensed aromatic group, or —NH— or —O—,
p and q, which are the same or different from each other, are integers having a value of from 0 to 10, with a value of 0 being excluded when X is either —NH— or —O—;
Y is —NH$_2$, —OH or —SH;

and wherein the polymeric organic matrix is based on a polymer obtained by reacting (1) a polymerized olefin, whose monomer has the formula:

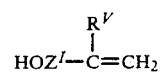

wherein:
$Z^I$ is

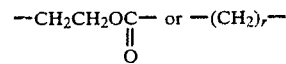

wherein r is an integer having a value of from 1 to 10, and
$R^V$ is either H or CH$_3$, with the proviso that $R^V$ is not CH$_3$ when $Z^I$ is —(CH$_2$)$_r$—,
with (2) a compound obtained by reacting 2,4-toluene-diisocyanate with a di-alcohol, a di-amine, a glycol, a tri-alcohol or a tri-amine having the formula:

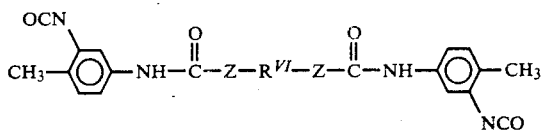

wherein:
$R^{VI}$ is —(CH$_2$CH$_2$O)$_m$CH$_2$CH$_2$—, wherein m is an integer having a value from 1 to 20,000;
or is —(CH$_2$)$_s$—,
wherein s is an integer having a value of from 1 to 20, or is:

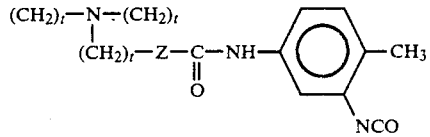

wherein
t is an integer having a value of from 1 to 10 and Z is —NH— or —O—, with the proviso that Z is not —NH— when $R^{VI}$ is —(CH$_2$CH$_2$O)$_m$CH$_2$CH$_2$—.

2. The ion sensor according to claim 1, wherein said polysiloxanic matrix is formed from aminoethyl-aminopropyltrimethoxy-silane or aminoethyl-aminomethylphenethyl-trimethoxy-silane.

3. The ion sensor according to claim 1, wherein the polymeric organic matrix is based on a polymer obtained by reacting 2-hydroxyethyl-methacrylate and a compound obtained by reacting 2,4-toluene-diisocyante and triethylene-glycol or triethanolamine.

4. The ion sensor according to claim 1, wherein said ionophore is an ionophore capable of forming selectively ion-permeable channels.

5. The ion sensor according to claim 4, wherein said ionophore is valinomycin or N,N-dibutyl-3,6-dioxa-octane-diamide.

6. The ion sensor according to claim 1, wherein said ion sensor is a potassium ion-selective sensor.

* * * * *